United States Patent [19]

Von Kesserü et al.

[11] 4,034,749

[45] July 12, 1977

[54] INTRAUTERINE CONTRACEPTIVE DEVICE

[75] Inventors: Istvan Von Kesserü, Lima, Peru; Gerhard Laudahn, Berlin, Germany; Barbara Mühe, Berlin, Germany; Gisela Schöpflin, Berlin, Germany

[73] Assignee: Schering Aktiengesellschaft, Berlin & Bergkamen, Germany

[21] Appl. No.: 640,545

[22] Filed: Dec. 15, 1975

Related U.S. Application Data

[63] Continuation of Ser. No. 530,385, Dec. 6, 1974, abandoned.

[30] Foreign Application Priority Data

| Dec. 6, 1973 | Germany | 2361206 |
| Jan. 18, 1974 | Germany | 2402882 |
| June 1, 1974 | Germany | 2426944 |

[51] Int. Cl.² ......................................... A61F 5/46
[52] U.S. Cl. ................................ 128/130; 128/260
[58] Field of Search .......................... 128/127–131, 128/260

[56] References Cited

U.S. PATENT DOCUMENTS

| 3,374,788 | 3/1968 | Rosenthal | 128/130 |
| 3,507,274 | 4/1970 | Soichet | 128/130 |
| 3,620,212 | 11/1971 | Fannon et al. | 128/130 |
| 3,645,258 | 2/1972 | Massouras | 128/130 |
| 3,675,648 | 7/1972 | Phariss et al. | 128/130 |

*Primary Examiner*—Lawrence W. Trapp
*Attorney, Agent, or Firm*—Millen & White

[57] ABSTRACT

A Y-shaped medicated contraceptive IUD for human use having a pair of elastomeric arms rounded at the ends thereof to facilitate insertion and removal, and a base containing protrusions to aid in gripping of the device by the cervix muscles. The device is adaptable to virtually any size human uterus and shows fewer side effects and spontaneous expulsions than known IUD's.

24 Claims, 1 Drawing Figure

INTRAUTERINE CONTRACEPTIVE DEVICE

This is a continuation of application Ser. No. 530,385, filed Dec. 6, 1974 and now abandoned.

BACKGROUND OF THE INVENTION

This invention relates to a human intrauterine contraceptive device containing a contraceptionally active medicinal agent.

Contraceptives containing a medicinal agent for intrauterine application (IUD's) make available safely effective contraceptives without ovulation inhibition by using smaller quantities of active medicinal agent than are required when administered by way of the gastrointestinal tract. The human organism is accordingly burdened only with a minimum of medicinal agent and thus treated more gently; subjective as well as objective side effects are greatly reduced in comparison with other birth control techniques.

The use of IUD's widely differing with respect to material, configuration and effectiveness has been known for a long time. An early contraceptive means, to be used as an intrauterine device, was developed in 1920 by GRAEFENBERG with the utilization of a wire copper-silver alloy. The activity mechanism of presently known IUD contraceptive devices, however, has not yet been extensively clarified or fully understood.

Various synthetic resins, e.g. nylon, polyethylene, polyethylene/vinyl acetate, etc. have been employed in the pure form or with the addition of an X-ray contrast agent such as barium sulfate to obtain a great variety of IUD's. These devices, however, are relatively bulky and voluminous with respect to the typical dimensions of the uterine cavity, e.g. the MARGULIS coil of U.S. Pat. No. 3,200,815, German Patents 1,416,942 and 1,441,359; BIRNBERG's bow described in U.S. Pat. No. 3,253,590; the "Saf-T-Coil" of U.S. Pat. Nos. 3,234,938 and 3,374,788; and LIPPE's loop shown in U.S. Pat. No. 3,250,271.

All T-shaped devices have the common disadvantage that they cannot be sterilized in the applicator, due to the insufficient memory characteristic of the synthetic resin material. Insertion of the device into the applicator is hardly possible under aseptic conditions, since the device and the applicator are not adapted to each other in a suitable manner. Furthermore, the device and applicator together can lead to injuries during application, since the collapsed device and the upper rim of the insertion tube have sharp edges. The DALKON Shield and the applicator developed for this device are designed so that the insertion of the contraceptive is possible only with strong dilatation of the cervical canal.

The T-shaped contraceptive device of U.S. Pat. No. 3,533,406, the DALKON shield described in DOS (German Unexamined Laid-Open Application) 1,956,701 and LIPPE's LOOP D represent currently available intrauterine contraceptives made of a synthetic resin material which are smaller in circumference and volume than the aforementioned earlier devices. The reliability of these contraceptives can be enhanced by the application of metallic copper on the surface of the device; see Zipper, Amer. J. Obst. Gynec. 105, 1274-1278 (1969) and Jecht et al, Contraception 7 (5):381 (1973). Active medicinal agents such as pulverized copper or steroid hormones with a progestational gestagenic activity can be dispersed in the synthetic resin material. One kind of DALKON Shield, for example, contains copper distributed in highly dispersed form in the synthetic resin carrier. The COPPER-T and COPPER-7 devices of U.S. Pat. No. 3,563,235 are partially provided with a copper winding, while the COPPER TCu 220 C device of U.S. Pat. No. 3,533,406 is covered partially with copper sheaths.

The reliability of the contraceptive effect exhibited by intrauterine devices provided with copper on their surfaces can be further enhanced by the additional application of zinc or silver, see for example U.S. Pat. No. 3,563,235; Zipper et al., Amer. J. Obst. Gynec. 105:529-523 (1969a); and Zipper et al., Human Fertility Control Through the Use of Endouterine Metal Antagonism of Trace Elements in Control of Human Ferility, Nobel 15, Almquist & Wiksell, Stockholm (1971), page 199.

After application of intrauterine contraceptives containing medicinal agents, such as TCu 200 or TCu 220 C, of contraceptives containing copper and zinc, or of a device containing progesterone (German Pat. No. 2,247,949) or dl-11 β-ethyl-17 α-ethinyl-17 β-hydroxy-gon-4-3n-3-one, reduced pregnancy rates are observed as compared to the intrauterine contraceptives which are manufactured solely of a synthetic resin material.

Intrauterine contraceptive devices consisting of a synthetic resin article and a silicone rubber capsule containing a medicinal agent connected thereto and are also known for use in the uterine cavity, e.g. see Int. J. Fert. 15:210 (1970). These medicine-containing IUD's however, just as the medicine-free devices of the same configuration, lead to undesired side effects such as bleeding and pain as has been reported by Fortier et al., J. Amer. Obst. Gynec. 115 (3):291-297 (1973); Tatum, Contraception 6 (3):179-189 (1972); Mishell et al., Amer. J. Obst. Gynec. 116 (8):1092-1096 (1973).

The most frequent side effects of conventional IUD's are hemorrhaging and pain. The number of intrauterinely applied contraceptive devices removed due to these complaints is greater in connection with the bulky synthetic resin devices than for the less bulky units, such as the DALKON Shield, T-shaped contraceptives, or LIPPE's LOOP D.

Side effects and removal necessitated by these side effects, as well as spontaneous expulsions of IUD's manufactured from a synthetic resin material are, however, due not only to unfavorable configurations and dimensions of these devices. Further essential factors in this connection are the elasticity and hardness of the synthetic resin material. Devices made of a plastic material too low in elasticity and too high in hardness often cause pains and cramps. Accordingly, these devices must be manufactured in various sizes, corresponding to the dimensions of the uterine cavity. Contraceptives made of a synthetic material that is too soft can jam by twisting in the uterus and are then often expelled spontaneously, or they can occasionally penetrate the uterus musculature. Fragments and intact devices of such IUD's, once having penetrated through the wall of the uterus, enter the abdominal cavity and can result in additional injuries such as strangled intestinal loops.

In general, less bulky intrauterine contraceptives made of a plastic material have been found to cause fewer side effects and spontaneous expulsions than bulky synthetic resin devices. The absolute number of undesired side effects and spontaneous expulsions is, however, still intolerable in both types for an intrauterine contraceptive. Even in the less bulky intrauterine contraceptives, one observes side effects such as the occurrence of dysmenorrhea, metromenorrhagias and leukorrhea associated with long-term pain and temporary cramp-like pain; see, for example, Ostergard et al., Contraception 4 (5):313–317 (1971); Portruff et al., Am. J. Obst. Gynec. 114 (7):934–937 (1972); Taylor et al., Obst. Gynec. 41 (3):404–413 (1973); Buchmann, Fert. Steril. 21 (4):348–355 (1970). The pregnancy rate, calculated according to the life-table method [Tietze, Intra-Uterine Contraception, Recommended Procedures for Data Analysis Studies in Family Planning, No. 18 (Suppl.), The Population Council, New York, 1967], is so high with the use of these contraceptives that the reliability of their effectiveness does not attain the reliability of conventional orally administered contraceptive hormones as reported by Fuchs et al., Contraception 5 (2):119–127 (1972); by Baeyertz, Austr. N. Z. J. Obst. Gynec. 11:117–121 (1971) and by Davis, Amer. J. Obst. Gynec. 114 (1):134–151 (1972). Buchmann, in Fert. Steril. 21 (4):384–355 (1973) has also reported that perforations of the uterine wall by this type of contraceptive device are frequently observed.

Rigidly shaped intrauterine contraceptive devices can break within the uterus when subjected to corresponding alternating bending stresses. The fragments can be expelled unnoticeably or, just as the intact devices, can penetrate the uterine wall and enter the abdominal cavity; see Last, J. Obst. Gynec. Brit. Commonw. 79 (2):190–191 (1972) and Domany et al., British Med. J. 1:549 (1973).

Disadvantages inherent in conventional IUD's include spontaneous expulsions, the occurrence of pregnancies, or the necessity for removing the device because of medical reasons. Removal of the IUD due to side effects is especially frequent at the beginning of the usage period, as reported by AVERY, Rep. Popul. Family Plan 4 (6):139 (1973).

In addition to the large number of necessary removals of these contraceptive articles due to medically intolerable side effects, spontaneous expulsions are reported by Fortier et al., Amer. J. Obst. Gynec. 115 (3):291–297 (1973); Johannisson, Contraception 8 (2):99–112 (1973); Snowden et al., Contraception 7 (2):91–104 (1973); and Horowitz, Contraception 7 (1):1–10 (1973). Spontaneous expulsions are observed with the DALKON Shield described in DOS (German Unexamined Laid-Open Application) 1,956,701 and Ostergard et al., Obst. Gynec. 41 (2):257–258 (1973), and with T-shaped contraceptives, e.g. copper-7; Newton et al., Lancet 1972/II No. 7784, 951–954; Bernstein et al., Contraception 6 (12):99–107 (1972), even though these devices are shaped with abutments arranged in opposition to the expulsion direction to avoid an ejection movement of the device, see Jones et al., Brit. Med. J. 3:143 (1973). In the DALKON Shield, these abutments are affixed to a ring in the form of lateral projections shaped like fingers and spikes. Intrauterine contraceptive devices shaped in this way inherently include the danger of uterus injuries not only during application, but during the period of use, see Koetsawang, Contraception 7 (4):327–332 (1973); Johannisson, Contraception 8 (2):99–112 (1973); Lehfeldt et al., Obst. Gynec. 37 (6):826–831 (1971); Brooks et al., Amer. J. Obst. Gynec. 113 (1):104–106 (1972); Sprague et al., Obst. Gynecol. 41 (1):80–82 (1973); Rienprayura et al., Contraception 7 (6):515–521 (1973), and also during removal, e.g. see Snowdon et al., Contraception 7 (2): 21–104 (1973). KAMAL et al., in Fert. Steril. 24 (3):165–169 (1973) state that minor injuries to the uterine wall, caused by the two horizontal ends of the T-shaped contraceptive of U.S. Pat. No. 3,533,406 which anchor the device within the uterine wall, are even advantageous for the effectiveness and fixation of the contraceptive device.

In the copper-containing IUD's such as COPPER-T, the copper wire under appropriate mechanical stress can break or can partially detach itself from the synthetic resin component. Such fragments of the copper wire can easily lead to injuries, as these fragments can penetrate the wall of the uterus and progress into the abdominal cavity and can be difficult to locate. In connection with the COPPER-TCu 220 C IUD, the danger of a uterine wall perforation with a subsequent separation of the copper cylinders and the danger that the copper cylinders remain in the abdominal cavity are especially great.

The heretofore customary IUD's are also disadvantageous with respect to their total weight and/or their weight distribution within the device, favoring a spontaneous expulsion. For example, the COPPER-TCu 220 C device weighs 612 mg. and one type of the LIPPES LOOP weighs 665 mg. Metal-containing IUD's such as that described in DOS 2,207,939, are readily spontaneously expelled due to the poor weight distribution within the device, with the metal rings are fixed in position exclusively at the shank of the synthetic resin component.

Other IUD's, for example in accordance with German Pat. No. 1,441,359 or DOS 2,207,939, have an extension of the coil to be applied by the intrauterine method, with the coil extension reaching from the uterine cavity through the cervical canal into the vagina. These devices are uniformly manufactured of a synthetic resin material. The synthetic resin best suited for the formation of the coil is, however, too rigid for the section located intracervically and intravaginally. Therefore, many side effects such as cramp-like pains and bleeding are observed for these IUD's which extend into the cervical canal; see WILLSON, Amer. J. Obst. Gynec. 92:62 (1965). A consequence of the uterine cramps is often unnoticed spontaneous expulsions and subsequent pregnancies.

Another disadvantage of conventional IUD's which contain medicinal agents is that the release of nonmetallic effective agents therefrom takes place, over the long-term duration, without the regularity required to maintain the contraceptive activity and without the dispensation of specific levels adjusted to predetermined limits. The manufacture of great numbers of these types of contraceptives is furthermore difficult from a technical viewpoint and can be accomplished only with the aid of a large number of different manufacturing steps.

The critical population problems of many countries have been magnified by the recent oil crisis. As it takes over a generation to achieve population stability once a zero population growth rate has been reached, there is an urgent need for contraceptive devices which are reliably effective without the aforementioned disadvantages of heretofore available IUD's. The present invention fills such needs.

OBJECTS OF THE INVENTION

Accordingly, it is a general object of this invention to provide an improved human intrauterine contraceptive device.

A more specific object of the present invention is to provide an IUD shaped and dimensioned to be usable without physical or psychological impairment in nulliparae, nulligravidae, multiparae and multigravidae uterine cavities.

Another object of this invention is to provide an IUD of a design which cannot jam by twisting within the uterus, even under the stresses of great uterine motility in a small uterine cavity.

A further object of this invention is to provide an IUD which is continuously useable over a time interval of several years without inhibiting or impairing fertility during the period of usage.

An additional object of this invention is to provide an IUD substantially free of side effects such as dysfunctional bleeding, infections, cramp-like pain, translocation perforations and migrations, and spontaneous expulsions.

Yet another object of this invention is to provide an IUD which can safely and easily be inserted aseptically, used and readily located without mechanical injury to the uterus, and extracted without injury to the uterus.

A still further object of this invention is to provide an IUD having a balanced combination of shape, weight, weight distribution, hardness and flexibility to safely yet gently resist mechanical stresses within the uterus.

Yet an additional object of this invention is to provide such an IUD which can be aseptically inserted into the uterus in a painless manner without appreciable dilation the cervical canal, and an IUD applicator for use therewith.

Yet another object of this invention is to provide a sterilizable, integrally formed IUD having the above properties which can be produced on a commercial scale in a simple manner.

A more particular object of this invention is to provide an IUD having a progestationally medicated appendage having a quieting effect on uterine activity during the first few months of use, whereby early expulsions are greatly reduced.

Upon further study of the specification and appended claims, further objects and advantages of this invention will become apparent to those skilled in the art.

SUMMARY OF THE INVENTION

Briefly, the above and other objects are attained in one aspect of the present invention by providing, in an intrauterine contraceptive device for use in humans utilizing a physiologically acceptable support for a physiologically acceptable and contraceptively effective medicinal agent, the improvement wherein the support comprises a composite structure of a plurality of alternating balls and rods adapted for retention in the uterus, said structure weighing not more than 0.5 g. and being composed of a synthetic resin having an elasticity of 900–2,900 kp/cm$^2$, a tensile strength of 50–700 kp/cm$^2$, and a hardness of Shore A 35–A85.

BRIEF DESCRIPTION OF THE DRAWING

The above and the objects, features and advantages of this invention will become more fully apparent to those skilled in the art to which this invention pertains from the following Detailed Discussion, taken with the annexed Drawing wherein the FIGURE is a schematic plan view, approximately to scale, of an IUD an applicator therefor constructed in accordance with the principles of the present invention.

DETAILED DISCUSSION

The above and other objects are attained according to this invention by providing that a composite IUD consisting of rods and several balls of a synthetic resin of high elasticity, tear resistance, and average hardness with a maximum weight of 0.5 g. and which includes one or more active medicinal agents, optionally with an intracervical appendage of a synthetic resin, preferably a low-temperature vulcanizing (LTV) silicone elastomer, in the form of a thread.

The IUD's of the present invention generally exhibit a total volume 150–300 mm$^3$ and a total surface area of 250–450 mm$^2$, of which about 50% is of the spherical surfaces. The device as a whole has a density of 1.0–2.4, preferably 1.1–2.2 and a weight of less than 500 mg., generally 150–450 and preferably 200–430 mg.

Suitable elastomers are nontoxic and physiologically acceptable, and have an elasticity according to ASTM D 747 and D 638 of 900 to 2,900 kp/cm$^2$, preferably 1,000–2,750 kp/cm$^2$; an elongation at break according to ASTM D 638 of 180–550%, preferably 250–480 for silicone elastomers and 130–1,000, preferably 250–900 for thermoplastics; and a hardnss degree Shore according to ASTM D 676 of A 35–85, preferably A 40–75 for silicone elastomers and D 40–70, preferably D 45–60 for thermoplastics.

Figure 1:
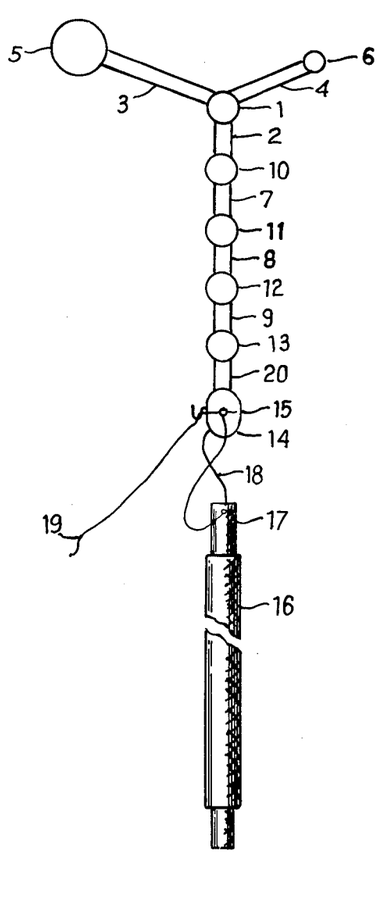

This device has, with a total length of 3–4 cm., a Y-like contour. Starting with intersecting sphere 1 having a diameter of 2.5–3.0 mm., three round rods 2–4 of varying lengths and each with a diameter of 1.0–1.5 mm. intersect sphere 1 and each terminate in balls. Rod 3 extends outwardly from sphere 1 at an obtuse angle of 100°–130°, preferably 110°–120° to the third rod 2 for a length of about 0.8–1.2 cm. and terminates in sphere 5 having a diameter of about 4–5 mm. Rod 4 extends, preferably but not necessarily in substantially the same plane as rods 1 and 2, outwardly from sphere 1 at an obtuse angle of 100°–130°, preferably 110°–120° to the third rod 2 for a length of about 0.5–0.8 cm. and terminates in sphere 6 having a diameter of about 1.5–2.0 mm. The combined diameters of rods 3 and 4 are less than the diameter of sphere 1, and the relative lengths thereof are such that retraction of the IUD into applicator 16 bends rods 3 and 4 into approximate axial alignment with rod 2, with the smaller sphere 6 resting along the length of rod 3 and tangential to or preferably but not necessarily inwardly spaced from the larger sphere 5, with the combined axial length of rod 4 and sphere 6 being no greater than the length of rod 3. The relative size of the various spheres is thus sphere 5 the largest and sphere 6 the smallest, with intermediate sized spheres disposed along the base of the Y. During insertion, sphere 5 gently dilates the cervix to the extent necessary to receive the entire device, and the elasticity of rods 3 and 4 enables them to assume the proper Y shape once the applicator has been withdrawn, as well as permitting deformation collapsing of the arm of the Y to facilitate removal when desired. In this connection, the shorter arm of the Y is easily collapsible, so that the resistance of the longer arm and sphere 5 thereon is overcome alone rather than together with the shorter arm. While the mechanical properties of spheres 1, 5 and 6 and rods 3 and 4 are thus of relatively greater importance than those of the various components comprising the base of the Y, which latter components aid in retaining the IUD within the cervix by providing a gripping surface for the cervix muscles, it is preferable that each segment of the Y be of the same material so that manufacture by simple injection molding is possible and to obtain a balanced weight distribution in the resultant IUD.

The presence of sphere 1 at the intersection of the arms and base of the Y is not mandatory so long as the intersection is similarly strengthened, but is preferred since in addition to reinforcing the Y intersection it provides a convenient means for attaching each of the three intersecting rods to a different surface, thereby better distributing mechanical stress on the intersection and facilitating independent movement of each rod within the uterus.

The third rod 2 is continued via a composite of four rods 7, 8, 9 and 20 and four balls 10–13 having a diameter of 2–3 mm. into a bean-shaped end piece 14 having a length of 4–5 mm. and a diameter of 2–3 mm. with a central bore 15 of a diameter of 0.5–1.5 mm. provided for the attachment of a thread 18 made of a suitable material, e.g. nylon or polyester. This thread serves as an indicator cord for simple testing of whether the contraceptive device is present.

A special embodiment of the contraceptive of this invention resides in that, through the central bore 15, additionally to the indicator thread 18, a further thread of a synthetic resin is provided as an intracervical appendage 19, this thread likewise containing a medicinal agent.

For the manufacture of the synthetic resin component for the contraceptives of this invention, conventional synthetic resins are utilized which, on the one hand, release nonmetallic medicinal agents disposed therein and, on the other hand, have sufficiently satisfactory mechanical properties, such as tear strength, elasticity, and cold-workability, and which can readily be molded to suitable shapes. Illustrative examples in this connection include but are not limited to polyethylene, polyethylene/vinyl acetate, ionomer resins (preferably derived from polyethylene), polyamides, polyether-ester elastomers on terephthalate basis, polyethylene glycol terephthalate, silicone rubber, etc. The plastics can be utilized either individually or in combination, e.g. by layered molding. The contraceptive medicinal agents incorporated into the intrauterine contraceptive devices of this invention are suitable metals, metal alloys, or nonmetallic drugs of natural or synthetic origin which are fixed onto the surface of the plastic component and/or are contained in the synthetic-resin base.

Suitable metallic medicinal agents include but are not limited to metals such as copper, silver, nickel or combinations thereof with one another, as well as combinations of the pure metals with the corresponding metal alloys. Metals and/or metal alloys can be dispersed uniformly in the entire plastic component only in certain parts thereof, or they can be applied partially and/or alternatingly onto the surface of the contraceptive device in a known manner.

The metallic medicinal agents are introduced into the interior or the surface of the plastic component in a conventional manner, e.g. by electroplating, vapor deposition, electroless deposition optionally with the aid of an adhesive agent, or by dispersion. The contraceptive activity is not substantially affected by the particular way in which the metal is deposited during the galvanic application of the metal or the metals, or by whether or not layers of various metals are placed one on top of the other. The layer thickness of the thus-applied metal is dimensioned with regard to the ductility of the metal layer so that the metal, in case the contraceptive device is subjected to high alternating bending stresses within the uterus, is not detached from the plastic element. For example, the copper layer plated on a device of this invention has a total weight of 177 mg and presuming a daily release rate of about 50 $\mu$g over 2 years, the remaining copper layer has still an average thickness of about 103 $\mu$m (141 mg), i.e., the remaining metal layer is not detached from the elastomer surface to such extent that cracks would occur.

In a specific form of application of the contraceptive, the metallic medicinal agent is applied to the balls 5, 6, 10, 11, 12, 13; the metal on each of the balls can be identical or different. The arrangement can be in groups or also in an alternating pattern. Especially advantageous is the alternating provision of copper and nickel.

The nonmetallic medicinal agents contained in the contraceptives of this invention are preferably compounds having hormonal activity, local anesthetics, and weakly alkaline buffer substances. Suitable such compounds are well known in the art and include but are not limited to $\Delta^4$-pregnene-3,20-dione (progesterone); d-13-ethyl-17$\beta$-ethinyl-17$\beta$-hydroxy-4-gonen-3-one (d-norgestrel) and the esters thereof; 17$\alpha$-ethinyl-19-nor-testosterone (norethisterone) and the esters thereof; 6-chloro-17-hydroxy-1$\alpha$,2$\alpha$-methylene-pregna-4,6-diene-3,20-dione (cyproterone) and the esters thereof; 3-methoxy-19-nor-17$\alpha$-pregna-1,3,5(10)-trien-20-yn-17-ol (mestranol); 18-methyl-19-nor-$\Delta^4$-pregnen-17$\alpha$-ol-3,20-dione-17$\alpha$-caproate; 3-hydroxy-1,3,5 (10)-trien-17-one (estrone); 17-acetoxy-6$\beta$,7$\beta$-epoxy-1$\alpha$,2$\alpha$-methylene-4-pregnene-3,20-dione; 4,6-dichloro-17-acetoxy-16$\alpha$-methyl-4,6-pregnadiene-3,20-dione; 17$\alpha$-hydroxy-6-methyl-pregna-4,6-diene-3,20-dione acetate (megestrol acetate), 19-nor-5$\alpha$-pregnane-3,20-dione; 3$\beta$-hydroxy-19-nor-5$\alpha$-pregnan-20-one; 19-nor-hydroxyprogesterone and the esters thereof; 6-chloro-17-hydroxy-pregna-4,6-diene-3,20-dione acetate (chlormadinone acetate); 1,3,5,(10)-estratriene-3,17$\beta$-diol (estradiol); 1,3,5 (10)-estratriene-3,16$\alpha$,17$\beta$-triol (estriol); 17$\beta$-hydroxy-4-androstein-3-one (testosterone) and the esters thereof; 21-hydroxy-5$\beta$-pregnane-3,20-dione and the esters thereof; 17$\alpha$-acetoxy-6$\alpha$-methyl-progesterone (medroxy-progesterone acetate); 10$\alpha$-pregna-4,6-diene-3,20-dione (dydrogesterone); 17$\beta$-estradiol; as well as lidocaine and novocaine, and triethanolamine, ethylenediaminetetraacetic acid disodium salt, and Sörensen's phosphate buffer.

The nonmetallic drugs can be dispersed homogeneously in the plastic component, optionally with the aid of a conventional galanic auxiliary agent, or they can be contained in a suitable quantity in individual parts of the contraceptive device with or without these auxiliary agents, for example as a core element in a part of the plastic body. Auxiliary agents well known in the art and include but are not limited to tensides, highly disperse strengthening fillers such as silicon dioxide, defrothers, solubilizers, resorption retardants, X-ray contrast agents, ferromagnetic substances to aid in locating the contraceptive, etc.

A preferred embodiment of the contraceptive device contains in homogeneous distribution 10–30 parts by weight d-13-ethyl-17α-ethinyl-17β-hydroxy-4-gonen-3-one (d-norgestrel) in 100 parts by weight of silicone rubber base strengthened with 10–40 parts by weight of a highly dispersed silicon dioxide and containing about 5% of barium sulfate, which rubber base vulcanizes at slightly elevated temperature, e.g. of 40°–80° C.

Another embodiment of the contraceptive device of this invention contains, in balls 5, 6, 10, 11, 12, 13, core pieces comprising 20–45 parts by weight of a mixture of 6-chloro-17-hydroxy-1α,2α-methylene-pregna-4,6-diene-3,20-dione acetate (cyproterone acetate) and lactose (1:1 to 1:2), wherein the synthetic resin body of this contraceptive is composed of 100 parts by weight of a physiologically acceptable polyethylene/vinyl acetate compolymer.

The medicinal agents contained in the thread-like appendage 19 are regularly released from the carrier material of synthetic resin at a level adjusted within predetermined limits over a restricted period of time, i.e. during the first few months of use of the contraceptive; thereafter, the contraceptive effect is due to the medicinal agent in the contraceptive device, which has proven to be effective by itself.

The appendage 19 can especially be used with all metal-containing, intrauterinely applied contraceptive devices which are suitable for joining according to the art to an intracervical thread-like medicine carrier, e.g. by knotting, cementing, welding, etc. Examples in this connection are especially contraceptives such as those known from U.S. Pat. No. 3,533,406; DOS 1,956,701; U.S. Pat. No. 3,563,235; and DOS 2,207,939.

The dimensions of the thread are selected so that the latter extends into the cervical canal, but not into the vagina. This medicine-containing thread preferably has a diameter of 0.2–1.0 mm. and a length of 1.0–5.0 cm. The content of active medicinal agent in the thread is 10% – 70%, preferably in 25–35%.

The nonmetallic medicinal agents contained in the thread-like intracervical appendage are compounds with hormonal activity, such as those previously mentioned compounds suitable as nonmetallic agents in the device per se. Examples in this connection are Δ⁴-pregnene-3,20-dione (progesterone); d-13-ethyl-17α-ethinyl-17β-hydroxy-4-gonen-3-one (d-norgestrel) and the esters thereof; 17α-ethinyl-19-nor-testosterone (norethisterone) and the esters thereof; 6-chloro-17-hydroxy-1α,2α-methylene-pregna-4,6-diene-3,20-dione (cyproterone) and the esters thereof; 3-methoxy-19-nor-17α-pregna-1,3,5(10)-trien-20-yn-17-ol (mestranol); 18-methyl-19-nor-Δ⁴-pregnen-17α-ol-3,20-dione-17α-caproate; 3-hydroxy-1,3,5(10)-trien-17-one (estrone), 17-acetoxy-6β,7β-epoxy-1α,2α-methylene-4-pregnene-3,20-dione; 4,6-dichloro-17-acetoxy-16α-methyl-4,6-pregnadiene-3,20-dione; 17α-hydroxy-6-methyl-pregna-4,6-diene-3,2-dione acetate (megestrol acetate); 19-nor-5α-pregnane-3,20-dione; 3β-hydroxy-19-nor-5α-pregnan-20-one; 19-nor-hydroxy-progesterone and the esters thereof; 6-chloro-17-hydroxy-pregna-4,6-diene-3,20-dione acetate (chlormadinone acetate); 15,16α-and 15,16β-methylene-17β-hydroxy-18-methyl-17α-ethinyl-4-estren-3-one; 17β-hydroxy-4-androsten-3-one (testosterone) and the esters thereof; 21-hydroxy-5β-pregnane-3,20-dione and the esters thereof; 17α-acetoxy-6α-methyl-progesterone (me-droxy-progresterone acetate); 1-α-pregna-4,6-diene-3,20-dione (dydrogesterone); etc.

Preferred are steroid hormones having progestational activity, such as α-norgestrel and progesterone, norethisterone, cyproterone acetate, norhydroxyprogesterone, 15,16α- and 15,16β-methylene-d-norgestrel.

The nonmetallic medicinal agents are homogeneously dispersed in the medicine-containing thread, optionally with the addition of conventional auxiliary agents, e.g. tensides, defrothers, solubilizers, resorption retardants such as highly disperse silicon dioxide, etc.

Especially suitable as synthetic resins for the production of the medicine-containing appendage 19 are conventional LTV silicone rubber binary compositions which can be prepared, for example, according to the process of U.S. Pat. No. 2,823,218. Especially advantageous are those materials comprising 89–91% linear dimethylpolysiloxane having a molecular weight of 25,000–45,000 and containing maximally 0.5 molar percent of methylvinylsiloxane units, and 9–11% of a cross-linking dimethylpolysiloxane, containing Si—H—bonds, with a molecular weight of 500–1,000, which can comprise up to 3 Si—H—bonds per molecule, which are catalyzed with platinum or platinum compounds, such as hexachloroplatinic acid (elastomer composition I); or those compositions comprising 85–89% of said linear dimethylpolysiloxane with maximally 0.5 molar percent, generally 0.1–0.5% methylvinylsiloxane units, 5–6% cross-linking dimethylpolysiloxane with Si—H—bonds, 5–10% of a dimethylpolysiloxane resin with a molecular weight of 20,000 – 30,000 having a cross-linking and strengthening effect and containing maximally 1.2 molar percent, generally 0.5–1.2% of methylvinylsiloxane units, catalyzed with a platinum-ethanol complex compound (elastomer composition II).

The contraceptives of this invention are superior to the conventional contraceptives in their long-term effectiveness, inasmuch as the pregnancy rate during application, determined on the basis of the life-table method, is markedly lower, and fewer spontaneous expulsions and other side effects occur. For example, the device according to Example 5 was administered to 200 women over the period of 1 year. A Pearl-Index of 1,2 was found.

The expulsion rate of the contraceptive devices of this invention is extraordinarily low, for example 5 expulsions during the tests with the device of Example 5 given above. Although the devices have no abutments which act against an expelling motion, nor do they have a shape making it possible to anchor them in the mucous membrane of the uterus or in the uterine musculature. In contrast to medicine-free intrauterine contraceptives, there is no need for providing a large contact surface between the device and the endometrium without an impairment of the effectiveness, since an improved effect is attained by the addition of active medicinal agents and/or medicinal agent combinations.

By the use of such LTV synthetic resins, which have not heretofore been customary for the production of intrauterine contraceptives, it is possible to prepare progestogen-containing contraceptives exhibiting, over several months up to a few years and longer, a drug release rate within the limits of the dosage required for intrauterine contraception. These contraceptive agents are usable independently of the size of a particular uterine cavity and thus suitable for substantially universal application. The devices are constructed so that they do not enter or even penetrate the uterine musculature.

The advantage of the contraceptive devices with the thread-like appendage according to this invention appear to result from the quieting effect of the progestogens acting favorably on the uterus (UFER, J., "Hormontherapie in der Frauenheilkunde", Hormone Therapy in Gynecology, publishers Walter De Gruyter, Berlin, 1972, p. 124). The physiological increase in motility of the uterus musculature, normally occurring after the introduction of a foreign body, is thereby reduced. This decreases the rate of early expulsions and, in dependence thereon, also the number of thus-incurred pregnancies. Consequently, the disadvantage of a higher reject quota in the first few months of use, heretofore existing for all intrauterine contraceptives, is eliminated, and the first critical phase during the usage of IUD's can be bridged.

The medicine-containing contraceptives of this invention are also of a shape advantageous for their administration. For application purposes, conventional insert tubes 16 are suitable, having, for example, an inside diameter of 3.5 mm. and a wall thickness of 0.5 mm., made of high-pressure polyethylene or other suitable synthetic resins. The contraceptive is introduced into the tube under aseptic conditions and enclosed within the tube until ball 5 is in abutment, with the indicator thread 18 attached to the eye 15 and the push-and-pull rod 17 connected thereto. The ball 5 of the device forms a spherical closure for the application unit consisting of the contraceptive and the applicator. Since the rim of the insertion tube is covered, primary injuries therefrom during application are excluded. Furthermore, the blunt spherical end with a diameter of 4–5mm. prevents a penetration of the uterine fundus during application. The application of the contraceptive device can readily be accomplished by an obstetrician. This can be done under aseptic conditions without anesthesia or the use of additional drugs or dilatation of the cervical canal, even in case of female patients who have never had a child, and without the triggering of cramp-like pains.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight.

EXAMPLE 1

A synthetic resin component, molded from a thermoplastic polyether-ester elastomer on the basis of terephthalate with a contour as illustrated in the FIGURE has the following dimensions: total length 3.6 cm.; ball diameter (5) 4.8 mm., (6) 1.5 mm., (1) and (10–13) 2.8 mm.; rod diameter (4) 1.3 mm., (2–3) and (7–9) 1.5 mm.; length of rods (3) and (4) 0.85 cm. and 0.65 cm., respectively; length of eye 4.5 mm.; diameter of the eye 2.8 mm.; total weight of the plastic article: 220 mg.

The surface of the balls of the plastic element is partially and alternatingly galvanized with copper and nickel, with the aid of an adhesive substrate. The balls 5, 6, 10, 11, 12, 13 are galvanically coated with nickel (layer thickness 100 $\mu$) and the balls 5, 11, 13 additionally with copper (layer thickness 100 $\mu$). Elongation at break: 200%; tensile strength: 365 kg/cm$^2$; Shore hardness: D 55.

EXAMPLE 2

Synthetic resin components having the dimensions indicated in Example 1 are formed from a thermoplastic synthetic resin material derived from polyethylene, this material containing carboxyl groups joined to the chain molecules of the polymer and being cross-linked with sodium ions. The balls 5–6 and 10–13 of the plastic component are chemically copper-plated on the surface with the use of an adhesive substrate containing highly disperse iron (layer thickness: about 0.5 $\mu$). Nickel is galvanically applied to the chemically deposited copper layer (coating thickness: 80 $\mu$). The balls 5, 11, 13 are additionally provided galvanically with a copper coating (layer thickness: 60 $\mu$).

EXAMPLE 3

75.0 g. of a thermoplastic polyether-ester elastomer on terephthalate basis, present as an extremely fine granular material, is uniformly mixed with 12.5 g. of highly disperse copper powder and 12.5 g. of highly disperse nickel powder. Contraceptive devices with the dimensions set forth in Example 1 are shaped from the mixture. The angle between the axes of the rods 3 and 4 is 123°.

EXAMPLE 4

60.0 g. of a catalyzed silicone rubber binary component mixture of the low temperature vulcanizing type (LTV) is combined with 40.0 g. of highly disperse silicon dioxide. Plastic elements having the dimensions disclosed in Example 1 are formed from the suspension by 1 hour of vulcanizing of the shaped composition at 110° C. The plastic elements are galvanically coated partially and alternatingly with copper and nickel on their surfaces, as described in Example 2. The angle between the axes of the rods 3 and 4 is 125°.

EXAMPLE 5

An intrauterine contraceptive containing a partial surface layer of alternatingly copper and silver is produced as follows: Synthetic resin components are formed from high-pressure polyethylene with the contour shown in FIGURE and with the following individual dimensions: total length 3.4 cm.; ball diameter (5) 4.6 mm., (6) 1.6 mm., (1), (10–13) 2.6 mm.; rod diameter (4) 1.2 mm., (2 and 3), (7–9) 1.6 mm.; length of rods (3) 0.9 cm., (4) 0.7 cm.; length of eye 4.5 mm.; diameter of eye 2.6 mm.

Silver is deposited reductively on the spherically shaped parts 5, 6, and 10–13 of the plastic component (layer thickness about 1 $\mu$). Copper is applied galvanically to this silver layer (layer thickness about 90 $\mu$); the surface of the balls 5, 11, and 13 is additionally galvanically coated with silver (layer thickness 70 $\mu$).

EXAMPLE 6

Plastic components are molded from a thermoplastic polyether-ester elastomer on terephthalate basis with the dimensions indicated in Example 5 and with the contour as shown in the FIGURE. The partial metallic coating of the plastic components, consisting of copper and silver in an alternating arrangement, is applied — as set forth in Example 2 — with the aid of an adhesive substrate and subsequent galvanizing. During this process, the balls 5, 6, and 10–13 are coated with a layer of copper having a thickness of 100 μ, and the balls 5, 11, and 13 are additionally coated with a layer of silver, thickness 75 μ, on the 100 μ copper layer.

EXAMPLE 7

Plastic components of a thermoplastic polyether-ester elastomer on tetraphthalate basis, having the contour as illustrated in the FIGURE and with the dimensions set forth in Example 1, are galvanically coated on the balls 6, 10, and 12 of the plastic component, after the application of conductive silver varnish of a thickness of 10 μ, with a nickel coating (layer thickness 90 μ) and, on the balls 5, 11, and 13, likewise over a layer of about 10 μ of conductive silver varnish, with a silver coating (layer thickness 80 μ) by means of the galvanic method.

EXAMPLE 8

35.0 g. of micronized d-13-ethyl-17β-ethinyl-17β-hydroxy-4-gonen-3-one and 5.0 g. of highly disperse barium sulfate are homogeneously mixed with 60.0 g. of extremely finely granulated high-pressure polyethylene (particle size about 500 μ). Contraceptives having the contour indicated in the FIGURE and with the dimensions set forth in Example 5 are formed from the mixture, for intrauterine use.

EXAMPLE 9

30.0 g. of micronized d-13-ethyl-17α-ethinyl-17β-hydroxy-4-gonen-3-one (d-norgestrel) is incorporated into a mixture consisting of 5.0 g. of highly disperse barium sulfate, 20.0 g. of highly disperse silicon dioxide, and 45.0 g. of catalyzed LTV silicone rubber two-component composition. The suspension is shaped and vulcanized for 1 hour at 110° C. to plastic components containing d-norgestrel, having the contour as shown in the FIGURE and the dimensions of Example 1. Elongation at break: 290%; tensile strength: 70 kg/cm².

EXAMPLE 10

Pressed components are shaped from a mixture of 50.0 g. of micronized progesterone and 49.1 g. of lactose with 0.1 g. of lubricating additive, with a diameter of 2 mm. and a radius of curvature of 3 mm. The pressed progesterone pieces are introduced as cores into the spherical parts 5 and 10–13 of an intrauterine contraceptive. The basic structure and dimensions of this contraceptive are as illustrated in the FIGURE and as described in Example 5, and the contraceptive is made up of a mixture of 5.0 g. of barium sulfate, 35.0 g. of highly disperse silicon dioxide, and 60.0 g. of catalyzed LTV silicone rubber binary composition by 1 hour of vulcanizing at 100° C. subsequently to the shaping step.

EXAMPLE 11

A homogeneous mixture of 40.0 g. of 6-chloro-17-hydroxy-1α,2α-methylene-pregna-4,6-diene-3,20-dione acetate with 59.8 g. of lactose and 0.2 g. of lubricant mixture*⁾ is compressed to shaped articles (diameter 2 mm., radius of curvature 3 mm.). These articles are introduced as cores into the balls 5 and 10–13 of an intrauterine contraceptive device, the basic structure of which is shown in the FIGURE and the dimensions of which are indicated in Example 5, made up of high-pressure polyethylene with the addition of 5% of barium sulfate.

*⁾ magnesium stearate

EXAMPLE 12

From the mixture described in Example 9, medicine-containing synthetic resin components are produced by molding and 2 hours of vulcanizing at 100° C. By successive extraction with respectively 10 ml. of 96% ethanol for a period of 90 minutes and 70%, 50%, 30%, and 10% strength ethanol for 30 minutes, intrauterine contraceptives are produced with d-norgestrel being accumulated in the core of the plastic component.

EXAMPLE 13

50.0 g. of micronized 17β-ethinyl-19-nor-testosterone enanthate is mixed homogeneously with 10.0 g. of highly disperse silicon dioxide, 5.0 g. of barium sulfate, and 35.0 g. of catalyzed LTV silicone rubber two-component composition. The mixture is shaped into a basic element with a form similar to a Y, having a rod diameter of 1 mm. and a total length of 3 cm. The component is vulcanized for 10 hours at 60° C. This basic element serves as the core piece of an intrauterine contraceptive with a contour as shown in the FIGURE. This medicine-containing basic element is encased with high-pressure polyethylene so that contraceptives are obtained having the dimensions indicated in Example 5.

EXAMPLE 14

30.0 g. of d-13-ethyl-17α-ethinyl-17β-hydroxy-4-gonen-3-one is combined with 10.0 g. of barium sulfate and 60.0 g. of extremely finely granulated polyethylene/vinyl acetate copolymer and formed to a Y-like basic element having a rod diameter of 1 mm. and a total length of 3 cm. This medicine-containing basic element is encased with a mixture consisting of 45.0 g. of highly disperse silicon dioxide, 10.0 g. of barium sulfate, and 45.0 g. of catalyzed LTV silicone rubber binary composition, thus obtaining the dimensions of Example 1 and the contour of the FIGURE. This element is then vulcanized by heating same for 1 hour to 100° C. Elongation at break: 600%; tensile strength: 211 kg/cm²; Shore hardness: D 35; modulus of elasticity: 1,270 kg/cm²; angle between the axes of the rods 3 and 4 is 126°.

EXAMPLE 15

A plastic component method of thermoplastic polyetherester elastomer on terephthalate basis, having the contour as illustrated in the FIGURE has the following dimensions: total length 3.6 cm.; ball diameter (5) 4.8 mm., (6) 1.5 mm., (1), (10–13) 2.8 mm.; rod diameter (4) 1.3 mm., (2,3),(7–9) 1.5 mm.; length of rods (3) and (4) 0.85 cm and 0.65 cm., respectively; length of eye 4.5 mm.; diameter of eye 2.8 mm.; total weight of the plastic component: 220 mg.

The surface of the balls of the plastic component is galvanized partially and alternatingly with copper and silver, with the aid of an adhesive substrate. The balls 5, 6, 10, 11, 12, 13 are galvanically coated with silver (layer thickness 100 μ), and the balls 6, 10, 12 are additionally galvanically coated with copper (layer thickness 100 μ).

EXAMPLE 16

Plastic articles having the dimensions indicated in Example 1 are molded from a thermoplastic polyethylene-derived resin material containing carboxyl groups joined by copolymerization to the chain molecules of the polymer and being cross-linked with sodium ions. The balls 5, 6, 10–13 of the plastic article are superficially copper-plated by a chemical method with the use of an adhesive substrate containing highly disperse iron (layer thickness: about 0.5 $\mu$). Silver is applied galvanically to the chemically deposited copper layer (thickness of silver layer: 80 $\mu$). The balls 6, 10, 12 are additionally galvanically coated with copper (layer thickness: 80 $\mu$).

EXAMPLE 17

75.0 g. of a thermoplastic polyether-ester elastomer on a terephthalate basis, provided as an extremely finely granulated material, is uniformly mixed with 12.5 g. of highly disperse copper powder and 12.5 g. of highly disperse silver powder. Contraceptives having the dimensions indicated in Example 1 are formed from this mixture.

EXAMPLE 18

60.0 g. of catalyzed silicone rubber two-component mixture of the low temperature vulcanizing type (LTV) is mixed with 40.0 g. of highly disperse silicon dioxide. Plastic components having the dimensions indicated in Example 1 are produced from the suspension by 1 hour of vulcanizing the shaped mass at 110° C. The plastic components are galvanically coated as described in Example 2 partially and alternatingly on their surfaces with copper and silver.

EXAMPLE 19

An intrauterine contraceptive containing on its surface a partial coating of copper and silver in an alternating arrangement is produced as follows: Plastic components with the contour shown in the FIGURE are prepared from high-pressure polyethylene, having the following individual dimensions: total length 3.4 cm.; ball diameter (5) 4.6 mm., (6) 1.6 mm., (1), (10–13) 2.6 mm.; rod diameter (4) 1.2 mm., (2 and 3), (7–9) 1.6 mm.; length of rods (3) 0.9 cm., (4) 0.7 cm.; length of eye 4.5 mm.; diameter of eye 2.6 mm.

The plastic surface is activated by treatment with an ionic palladium solution on the spherically shaped parts (5, 6, and 10–13) of the synthetic resin component. Copper is chemically deposited on this activated surface with a layer thickness of about 1–2 $\mu$. Thereafter, by conventional methods of plastic galvanization, about 80 $\mu$ of silver is electrolytically deposited on the surface, and the balls 6, 10, and 12 are additionally coated electrolytically with 100 $\mu$ of copper.

EXAMPLE 20

Synthetic resin components having the dimensions set forth in Example 5 and the contour illustrated in the FIGURE are molded from a thermoplastic polyether-ester elastomer on terephthalate basis. The partial metal coating of the plastic components, consisting of copper and silver in alternating succession, is chemically and electrolytically deposited — as described in Example 19 — on the ball surfaces of balls 5, 6, and 10–13, activated by means of an ionic palladium solution. The electrolytically deposited silver layer has a thickness of about 90 $\mu$, and the electrolytically deposited copper layer has a thickness of about 60 $\mu$.

EXAMPLE 21

Partially metallized plastic components of a thermoplastic polyether-ester elastomer on terephthalate basis with copper and silver in alternating arrangement and having the contour indicated in the FIGURE and the dimensions of Example 1 are chemically copper-plated (layer thickness about 1–2 $\mu$) after activation of the plastic surface with ionic palladium solution. Thereafter, 100 $\mu$ of silver and 80 $\mu$ of copper are successively deposited by electrolysis. With the aid of a suitable cover varnish, the metal coating on all rods, on the end piece 14, and on the central ball 1 is removed in a two-stage process; the metal coat on balls 5, 11, and 13 is completely preserved, and the coating on balls 6, 10, and 12 is retained except for the 80 $\mu$ copper layer.

EXAMPLE 22

3.0 g. of micronized d-13-ethyl-17$\alpha$-ethinyl-17$\beta$-hydroxy-4-gonen-3-one (d-norgestrel) and 70.0 g. of LTV silicone rubber binary composition (elastomer type I) are processed into a suspension which is free of air bubbles. The suspension is shaped into threads by means of a nozzle and vulcanized by heating for 2 hours to 100° C., thus obtaining a thread having a diameter of 0.5 mm. This thread is cut to a length of 4 cm., respectively; after attaching the thread to an intrauterine contraceptive according to the FIGURE a free length of 2 cm. still remains. The thread together with the contraceptive device is sterilized for 30 minutes under high-tension steam and then packaged under sterile conditions.

EXAMPLE 23

Analogously to Example 22, a thread is produced having the same dimensions, containing as a progestationally active steroid hormone 25% of 17$\beta$-acetoxy-17$\alpha$-ethinyl-4-estren-3-one (norethisterone acetate).

EXAMPLE 24

The intracervical thread is produced with the use of 40 parts by weight of extremely finely micronized progesterone which is mixed with 60 parts by weight of catalyzed LTV silicone rubber two-component composition (elastomer composition II), by shaping the progesterone suspension and then heating the article for 1 hour to 100° C. The thread has a length of 2.5 cm. and a diameter of 0.5 mm.

EXAMPLE 25

Analogously to Example 22, a thread is produced having the same length but with a diameter of 0.4 mm., containing as the progestationally active steroid hormone 30% of 7$\alpha$-hydroxy-19-norpregn-4-ene-3,20-dione (norhydroxyprogesterone).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a human intrauterine contraceptive device including a physiologically acceptable solid support, the improvement wherein:

said support is a Y-shaped synthetic resin body comprising:
  a. a first resiliently deformable projection suitable for insertion into the body of a human uterus, comprising a first projecting elastomeric support member terminating at the distal end thereof in a first blunt, enlarged member;
  b. a second resiliently deformable projection suitable for insertion into the body of a human uterus, comprising a second elastomeric support member terminating at the distal end thereof in a second blunt, enlarged member having a diameter less than the difference between the diameter of said first support member and that of said first blunt member, the length of said second projection being no greater than the length of said first support member, said first and second support members comprising the arms of said Y and each forming an obtuse angle at the intersection of said Y with respect to each other and with respect to the base of said Y, whereby said first and second support members can be deformed into substantially axial alignment with the base of said Y; and
  c. a cervical projection support member forming the base of said Y and having formed thereon a plurality of generally annular, longitudinally spaced protrusions to provide a gripping surface for cervix muscles.

2. An intrauterine device according to claim 1 wherein the external dimensions of said Y-shaped body have a length-to-width ratio of about 1.5:1.

3. An intrauterine device according to claim 2 having a total length of 3–4 cm.

4. An intrauterine device according to claim 1 having a safe and effective amount of a contraceptive medicinal agent carried by said solid support.

5. An intrauterine device according to claim 4 wherein said medicinal agent comprises copper and nickel.

6. An intrauterine device according to claim 4 wherein said medicinal agent comprises copper and silver.

7. An intrauterine device according to claim 4 wherein the medicinal agent is d-norgesterol homogeneously distributed in a silicone rubber synthetic resin.

8. An intrauterine device according to claim 4 wherein the medicinal agent is cyproterone acetate and the synthetic resin is a copolymer of ethylene and vinyl acetate.

9. An intrauterine device according to claim 4 further comprising an LTV silicon elastomer thread containing a medicinal agent attached as an intracervical appendage to said cervical projection.

10. An intrauterine device according to claim 9 wherein the medicinal agent in said thread is a progestationally active steroid hormone.

11. An intrauterine device according to claim 1 wherein said synthetic resin has an elasticity of 900 to 2,900 kp/cm$^2$; an elongation at break of 180 to 550% and a Shore hardness of A 35 to A 85.

12. An intrauterine device according to claim 11 wherein said projections radiate from a spherical reinforcing support member formed at the intersection of said Y.

13. An intrauterine device according to claim 12 wherein said blunt, enlarged members are spheres.

14. An intrauterine device according to claim 13 wherein said first projection comprises a rod having a length of 0.8–1.2 mm. and a diameter of 1.0–1.5 mm. and terminates in a sphere having a diameter of 1.5–2.0 mm.

15. An intrauterine device according to claim 14 wherein said second projection comprises a rod having a length of 0.5–0.8 mm. and a diameter of 1.0–1.5 mm. and terminates in a sphere having a diameter of 4–5 mm.

16. An intrauterine device according to claim 15 wherein said generally annular protrusions are spheres integrally formed about the axis of said rod.

17. An intrauterine device according to claim 16 wherein said spheres contain a medicinal agent comprising copper and nickel or silver.

18. An intrauterine device according to claim 17 wherein copper and nickel or silver are alternatingly applied to the surfaces of said spheres.

19. An intrauterine device according to claim 16 wherein said cervical projection comprises four spheres each having a diameter of 2–3 mm. and terminates at the distal end thereof in an apertured bean-shaped end piece having a length of 4–5 mm. and a diameter of 0.5–1.5 mm.

20. An intrauterine device according to claim 19 further comprising an LTV silicon elastomer thread containing a medicinal agent attached as an intracervical appendage to said cervical projection.

21. An intrauterine device according to claim 20 wherein the medicinal agent in said thread is a progestationally active steroid hormone.

22. An intrauterine device according to claim 1, wherein said support weighs less than 500 mg.

23. An intrauterine device according to claim 1, wherein said first and second support members can be deformed into said axial alignment with said support members enclosed by an imaginary cylinder encircling said base, said first enlarged member having a diameter greater than that of said imaginary cylinder.

24. An intrauterine device according to claim 1, wherein
  a. a safe and effective amount of a contraceptive medicinal agent is carried by said solid support;
  b. said support weighs less than 500 mg.;
  c. said second blunt, enlarged member has a diameter less than the difference between the diameter of said first support member and that of said first blunt member; and
  d. said first and second support members can be deformed into said axial alignment with said support members enclosed by an imaginary cylinder encircling said base, said first enlarged member having a diameter greater than that of said imaginary cylinder.

* * * * *